(12) United States Patent
Bolger et al.

(10) Patent No.: US 7,875,061 B2
(45) Date of Patent: Jan. 25, 2011

(54) VERTEBRAL OSTEOSYNTHESIS PLATE, OSTEOSYNTHESIS SYSTEM AND METHOD TO IMPLANT SUCH A PLATE

(75) Inventors: Ciaran Bolger, Bristol (GB); John Bolger, Rath Farnham (IE)

(73) Assignee: Spinevision S.A., Paris (FR)

( * ) Notice: Subject to any disclaimer, the term of this patent is extended or adjusted under 35 U.S.C. 154(b) by 1153 days.

(21) Appl. No.: 10/108,319

(22) Filed: Mar. 27, 2002

(65) Prior Publication Data
US 2003/0187441 A1    Oct. 2, 2003

Related U.S. Application Data

(63) Continuation-in-part of application No. 10/019,718, filed on May 15, 2002, now abandoned.

(30) Foreign Application Priority Data
Jul. 1, 1999    (FR) .................................... 99 08495

(51) Int. Cl.
*A61B 17/80* (2006.01)
(52) U.S. Cl. ...................................................... 606/280
(58) Field of Classification Search .................. 606/61, 606/69–70, 71, 246, 280, 281, 286; 403/7, 403/375, 399
See application file for complete search history.

(56) References Cited

U.S. PATENT DOCUMENTS

| 5,951,557 | A | * | 9/1999 | Luter ........................... 606/69 |
| 2002/0022843 | A1 | * | 2/2002 | Michelson .................... 606/70 |

FOREIGN PATENT DOCUMENTS

| DE | 42 01 043 | | 7/1993 |
| EP | 0 556 548 | | 8/1993 |
| EP | 0 705 572 | | 4/1996 |
| WO | WO 94/28813 | * | 6/1994 |

* cited by examiner

*Primary Examiner*—Eduardo C Robert
*Assistant Examiner*—David Comstock
(74) *Attorney, Agent, or Firm*—Bachman & LaPointe, P.C.

(57) ABSTRACT

The present invention relates to a vertebral osteosynthesis plate to maintain relative vertebral orientation correction using a correction instrument. The osteosynthesis plate has an overall rectangular shape and comprises at least four slots to insert, in each, fixation devices, wherein at least two of the slots opens onto a lateral edge of the osteosynthesis plate to enable positioning and fixation of the plate with no prior removal of the relative vertebral orientation correction instrument. The edge of the plate is defined by an edge located in the same direction as the longitudinal direction of the plate. The longitudinal direction of the plate is roughly identical to that of the direction of the spinal column.

15 Claims, 12 Drawing Sheets

VERTEBRAL OSTEOSYNTHESIS PLATE, OSTEOSYNTHESIS SYSTEM AND METHOD TO IMPLANT SUCH A PLATE

CROSS-REFERENCE TO RELATED APPLICATION(S)

This application is a continuation-in-part of U.S. Ser. No. 10/019,718, filed May 15, 2002, entitled VERTEBRAL OSTEOSYNTHESIS PLATE AND OSTEOSYNTHESIS SYSTEM, now abandoned.

BACKGROUND OF THE INVENTION

The present invention relates to the field of spinal osteosynthesis surgery. More specifically, it relates to a vertebral osteosynthesis plate intended to immobilise at least two adjacent vertebrae in relation to each other.

Such plates are generally cut out of a rigid or flexible biocompatible material, particularly metal, for example titanium. They comprise circular or oblong slots to insert fixation screws or vertebral implants formed by a threaded device.

For example, the French patent applications FR 2763828 or FR 2766353 disclose vertebral osteosynthesis systems using plates known in the prior art.

The French patent application FR 2737402, which discloses a prior cervical spine stabilisation device, intended to fix the vertebrae and restore a normal interbody space is also known. The system comprises a double curve rectangular plate, equipped with ovoid slots, and corporeal anchoring screws, and threaded locking plugs housed in the threading provided in the top part of the anchoring screw.

These osteosynthesis plates according to the prior art are difficult to fit. Indeed, the surgeon starts by correcting the spinal alignment with a temporary correction instrument comprising correction rods intended to be attached in the vertebrae, which obstruct the fitting of the plate and its fixation. If the correction instrument is removed before the definitive fixation of the plate, it is necessary to make adjustments of the plate alignment before the definitive fixation.

To remedy this drawback, the German patent application No. DE 4 201 043 proposed a vertebral osteosynthesis plate of a general rectangular shape comprising at least four slots to insert fixation means and two longitudinal slits opening onto a transversal edge of the plate, to enable positioning and definitive fixation of the plate with no prior removal of the relative vertebral orientation correction instrument.

The major drawback of this plate lies in the fact that the surgeon is obliged to make six holes: two holes to enable the use of the relative vertebral orientation correction instrument and four holes to attach the vertebral osteosynthesis plate.

In addition, the presence of longitudinal slits makes it necessary to increase the width of the osteosynthesis plate.

SUMMARY OF THE INVENTION

The purpose of the present invention is to propose a plate avoiding these drawbacks. For this purpose, the present invention relates to a vertebral osteosynthesis plate to maintain the relative vertebral orientation correction using a correction instrument, said osteosynthesis plate having an overall rectangular shape and comprising at least four slots to insert, in each, fixation means. The osteosynthesis plate according to the invention is characterised, in its broadest embodiment, in that at least two slots open onto a lateral edge of said osteosynthesis plate to enable positioning and fixation of the plate with no prior removal of the relative vertebral orientation correction instrument.

The lateral edge of the plate refers to an edge located in the same direction as the longitudinal direction of the plate, the longitudinal direction of the plate being roughly identical to the direction of the spinal column, where the osteosynthesis is performed. The lateral edge also comprises the corner located at an angle with the transversal edge.

In this way, when the surgeon has corrected the relative vertebral orientation using correction rods of the correction instrument implanted in the vertebrae, he is able to position the osteosynthesis plate such that the correction rods of the correction instrument are inserted in said opening holes and start fixing the plate, while leaving the correction rods in position.

Advantageously, the holes made to fix the correction rods of the relative vertebral orientation correction instrument are also used, after partial fixation of the osteosynthesis plate and removal of the correction rods of the correction instrument, for the complete fixation of the osteosynthesis plate.

Advantageously, at least one of the slots opening onto the lateral edge of the plate has a curved, "L" or other shape, comprising a first transversal segment opening onto the lateral edge of the plate extended by a second longitudinal segment oriented in a roughly longitudinal direction.

In this way, the plate according to the invention contributes actively, as soon as it is inserted between the instrument correction rods, to spinal support.

Therefore, the plate may comprise two "L" shaped opening slots or one "L" shaped opening slot and a second transversally oriented opening slot, or two transversally oriented opening slots.

The vertebral osteosynthesis plate preferentially comprises two curved, "L" or other shaped opening slots, comprising a first transversal segment opening onto the lateral edge of the plate extended by a second longitudinal segment oriented in a roughly longitudinal direction.

Also advantageously, at least one of the slots not opening onto the lateral edge of the plate comprises a second segment oriented in a roughly longitudinal direction, in order to enable the automatic post-operative compensation of the effects of the compression of the intervertebral space occupied, most frequently, by a bone graft.

Preferentially, the spacing of the slots opening onto the edge of the plate is equivalent to the interbody distance between N vertebrae, N being an integer greater than or equal to two.

According to an alternative, the plate also comprises at least one slot provided roughly on the median longitudinal axis to fix a bone graft or other interbody component.

According to a preferred alternative, the plate also comprises at least one fixation hole for a covering plate intended to cover said fixation means at least partially, after fixation, said covering plate being, preferentially curved and also preferentially comprising at least one fixation hole, or two fixation holes wherein at least is oblong to enable, by tightening the covering plate against the osteosynthesis plate, to adapt it to the osteosynthesis plate profile.

According to a particular embodiment of the invention, at least one of said slots to insert fixation means, comprises at least two insertion positions for fixation means: one surface insertion position wherein said fixation means are roughly slanting at a fixed angle with reference to said plate, and one in-depth insertion position wherein said fixation means have a slanting position at a variable angle.

The invention also relates to a vertebral osteosynthesis system comprising a plurality of vertebral osteosynthesis plates to maintain the relative vertebral orientation correction produced using a correction instrument, said osteosynthesis plates having an overall rectangular shape and each comprising at least four slots to insert, in each of the slots, fixation means, at least two slots opening onto a lateral edge of said osteosynthesis plate to enable positioning and fixation of the plate with no prior removal of the relative vertebral correction instrument, the spacing of the slots being specific to each plate to enable the selection of the surgeon of the plate comprising a slot spacing similar to the intervertebral distance of the vertebrae of the patient during the operation.

The invention also relates to a method to implant a vertebral osteosynthesis plate according to the invention, to maintain the relative vertebral orientation correction using a correction instrument comprising correction rods implanted temporarily in said vertebrae, said osteosynthesis plate having an overall rectangular shape and comprising at least four slots to insert, in each, fixation means, at least two slots opening onto a lateral edge of said osteosynthesis plate, wherein the plate is positioned and fixed, with no prior removal of the relative vertebral orientation correction instrument, such that the correction rods of the correction instrument are inserted into the slots opening on the lateral edge of said plate, the edge of the plate being defined by an edge located in the same direction as the longitudinal direction of the plate, the longitudinal direction of the plate being roughly identical to that of the direction of the vertebral column.

According to said method, preferentially, before the positioning and definitive fixation of the plate, a compression force is applied onto said vertebrae, using said correction instrument.

Also according to said method, before the positioning and fixation of the plate, the dimension of the vertebral osteosynthesis plate required for the fixation of said vertebrae inserted perfectly in the correction rods is read preferentially on a reading rule of said correction instrument.

The invention also relates to a correction instrument used to produce a compression or a distraction on said vertebrae comprising a spring-mounted catch mechanism co-operating with a rack comprising means used to invert it.

Therefore, the instrument used to adjust the correction rod comprises two positions: one distraction position and one compression position. The distraction position is used to work on the disk and insert the bone graft or the interbody cage instead of said graft. The compression position is used to compress the bone graft or interbody cage.

Advantageously, the compression of the bone graft or interbody cage is practically retained until the final positioning of the plate and its fixation screws.

BRIEF DESCRIPTION OF THE DRAWINGS

The invention will be understood more clearly on reading the description below, for purely explanatory purposes, of an embodiment of the invention, with reference to the appended figures.

DETAILED DESCRIPTION OF THE PREFERRED EMBODIMENTS

The vertebral osteosynthesis plate according to the non-restrictive example described with reference to FIG. 1 has an overall rectangular shape and comprises four slots 1, 2, 4, 5 to insert fixation means for the vertebral osteosynthesis plate, such as for example a bone fixation screw 20. A median slot 3 is used to fix a bone graft or any other interbody support material.

Figure 2:
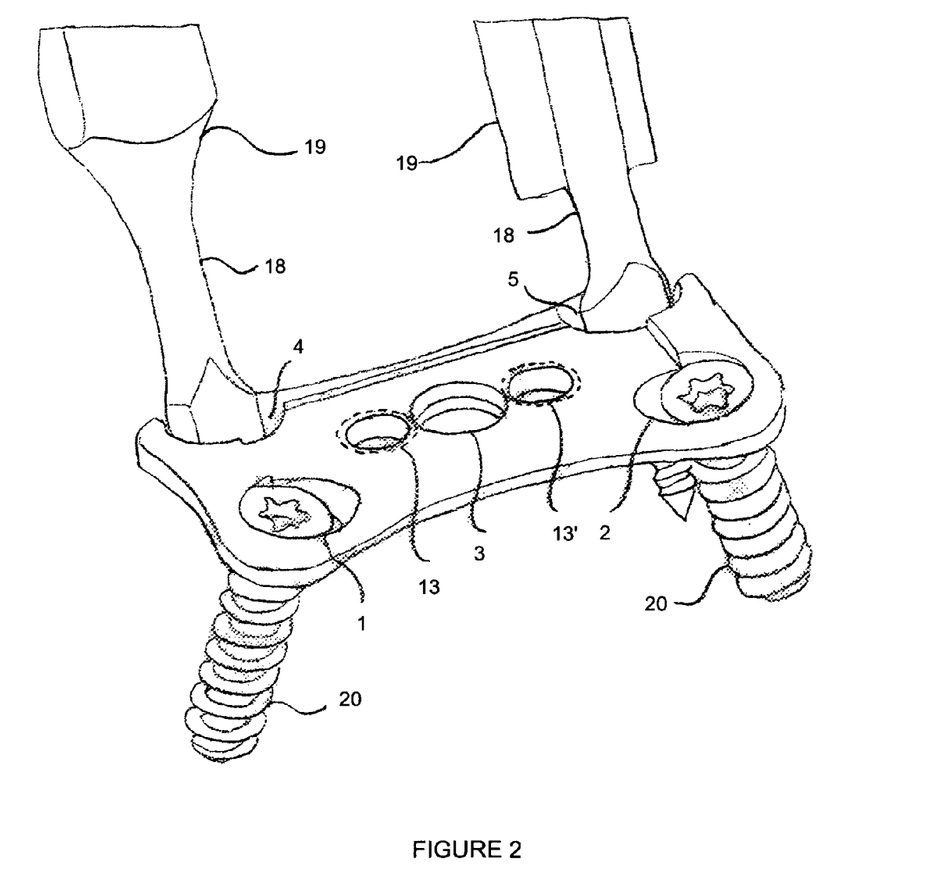
FIG. 2 represents a perspective view of the vertebral osteosynthesis plate during fixation, without the vertebrae.

Two slots 4, 5 open onto a lateral edge 6 of the plate to enable positioning and definitive fixation of the plate with no prior removal of the correction rods 18 of the relative vertebral orientation correction instrument 19, as illustrated in FIG. 2.

At least one of the opening slots 4, 5 and preferentially the two opening slots 4, 5 have a curved, "L" or other shape, comprising a transversal part opening onto the lateral edge 6 of the plate with, respectively, two notches 7, 8, a first transversal segment respectively 9, 11 extending in a transversal direction, perpendicular to the lateral edge 6, and a second longitudinal segment respectively 10, 12 extending in a roughly longitudinal direction G.

In addition, the slots 1, 2 are oblong.

The screw pitch enabling the fixation of the correction rods 18 of the correction instrument 19 in the vertebrae is of course, preferentially, roughly identical to that of the fixation screws 20.

Figure 1:
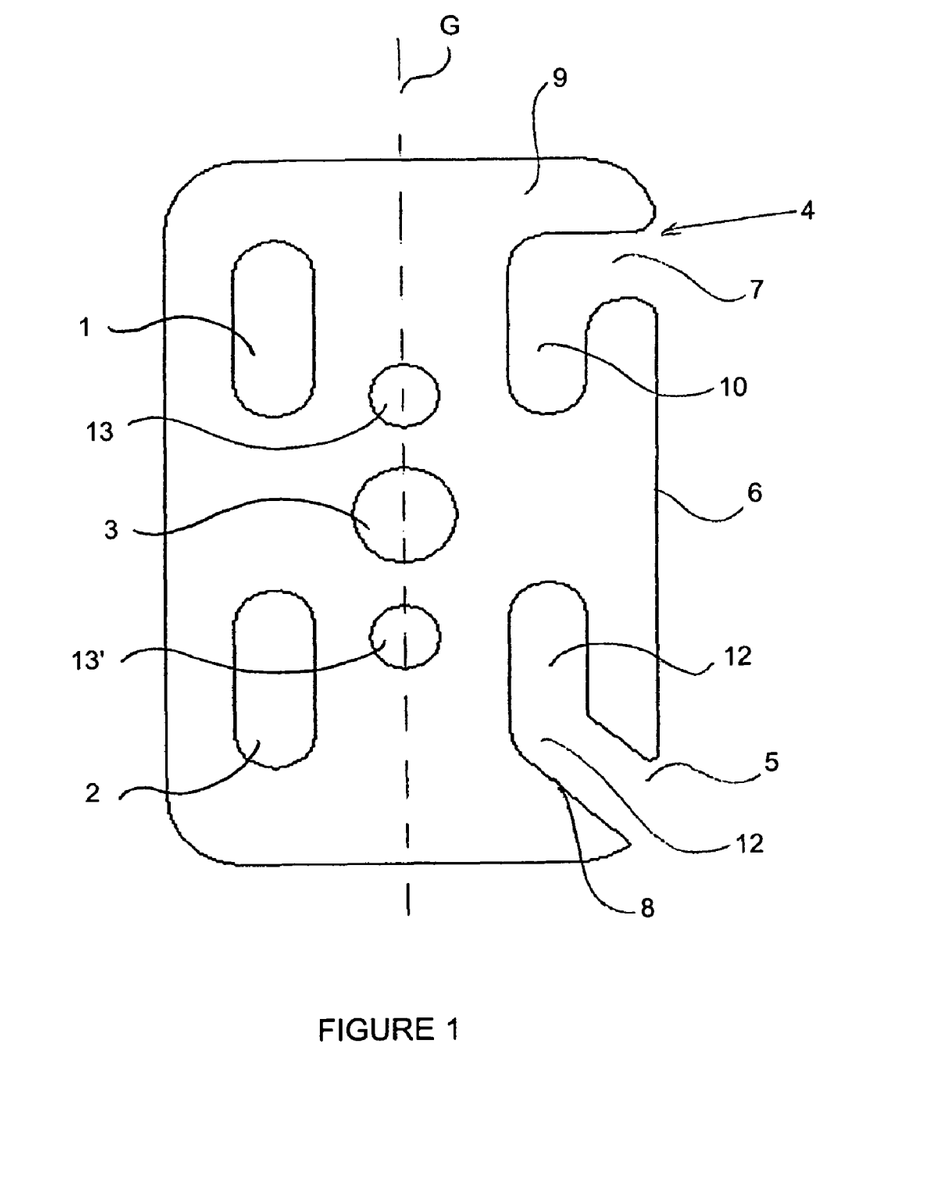
FIG. 1 represents a schematic view of a vertebral osteosynthesis plate according to the invention.
Figure 3:
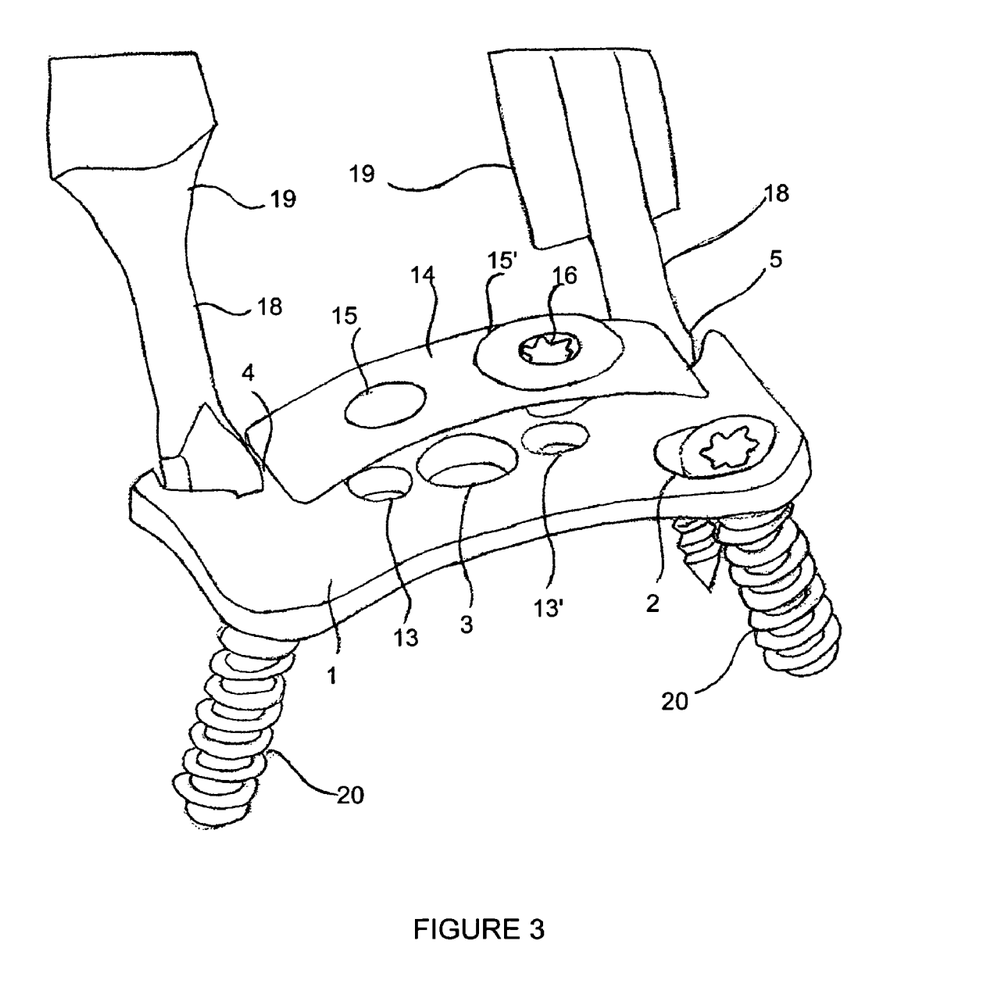
FIG. 3 represents a perspective view of the vertebral osteosynthesis plate in FIG. 2 equipped with a covering plate.

Preferentially, the plate according to the invention also comprises at least one fixation hole 13, 13' for a covering plate 14, as illustrated in FIGS. 1 to 3.

The covering plate 14 comprises at least one fixation hole 15, 15' intended to co-operate respectively with the fixation holes 13, 13' in order to enable the insertion of the fixation screws 16, 16' of the covering plate 14 on the vertebral osteosynthesis plate. (The screw 16' is not shown in FIG. 3 in order to maintain a sufficiently clear and precise representation).

The covering plate 14 is intended to cover all the fixation screws. The covering plate 14 has in the longitudinal section a curved shape in order to prevent the loosening of the screws 16, 16', by means of a spring effect and in order to adapt it to the curved shape of the osteosynthesis plate. To improve the latter effect, at least one of the fixation holes 15, 15' is oblong.

The covering plate 14 prevents the loosening of the screws 16, 16' by means of a spring effect, but does not fasten the fixation screws 20 completely, since they can still move in the second longitudinal segments of the slots 1, 2, 4, 5, in order to enable automatic compensation of intervertebral space compression effects.

Preferentially, the covering plate 14 is positioned in a housing provided on the surface of the osteosynthesis plate.

Figure 4:
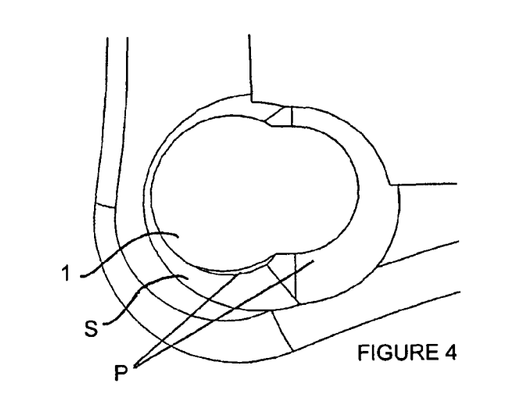
FIG. 4 represents a partial top view of a two-insertion position slot of the vertebral osteosynthesis plate according to the invention.
Figure 5:
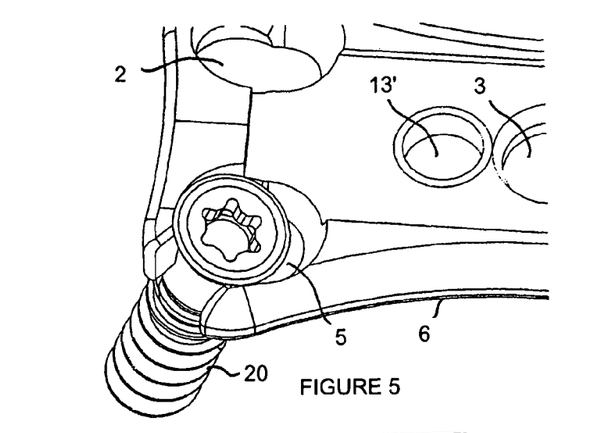
FIGS. 5 and 6, respectively, represent a partial top view of both positioning options, on the surface or in depth, of the bone fixation screws in a slot of the vertebral osteosynthesis plate according to the invention.
Figures 6, 7:
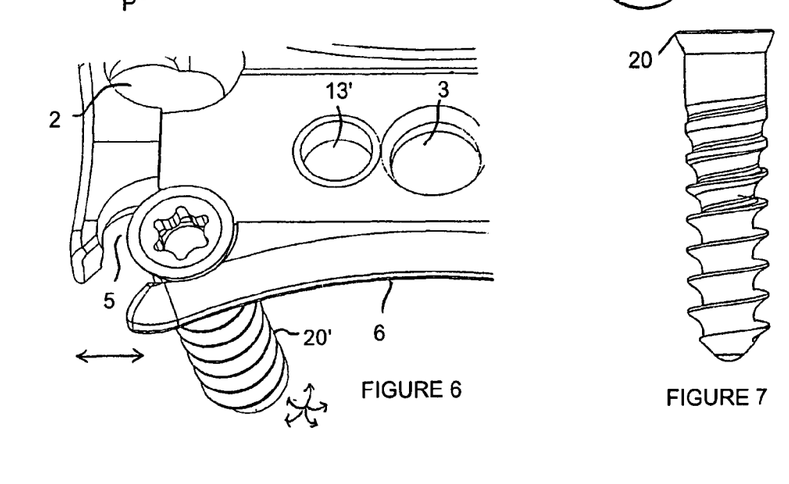
FIGS. 7 and 8, respectively, represent a front view of the two fixation screws, which may be positioned, on the surface or in depth in a slot of the vertebral osteosynthesis plate according to the invention with two insertion positions.

According to a specific embodiment, at least one of said slots 1, 2, 4, 5 to insert fixation means, as illustrated in FIG. 4, comprises at least two insertion positions S and P of fixation means: a surface insertion position S wherein said fixation means are roughly slanting at a fixed angle with reference to said plate, as illustrated in FIG. 5 and an in-depth insertion position P wherein said attachment means have a slanting position at a variable angle, as illustrated in FIG. 6.

Figure 8:
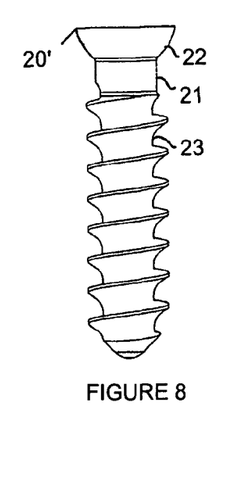

For fixed angle tightening of the fixation means in the surface insertion position, it is necessary to choose a conventional bone fixation screw 20, as illustrated in FIG. 7, while for variable angle tightening also allowing translation of the attachment means in the in-depth insertion position, it is necessary to choose a bone fixation screw 20' comprising a head 22 wherein the bottom face is rounded and comprising a part with a restricted section 21 positioned between the head 22 and the part comprising the screw pitch 23, as illustrated in FIG. 8.

The use of the plate according to the invention is as follows:

The vertebrae are equipped with correction rods 18 in order to enable vertebral realignment with a correction instrument 19 and the intervertebral disk is removed.

To position said correction rods precisely on the spinal column, the use of a suitably sized plate may be used as a guide. This "phantom" type plate is considered in this case as an instrument. As explained above, since the plate is to be attached onto the correction rods, the initial position of said plate directly involves the final position of the implanted plate.

This preliminary positioning of the correction rods then used as a guide makes it possible to plan the final position of the plate for the surgeon before working on the disk. The size of the "phantom" plate is not obligatorily that of the implanted plate depending on the thickness of the bone graft or the interbody cage.

The bone graft or interbody cage may then be inserted and the graft or interbody cage may be compressed if required using the correction instrument.

Figure 9:
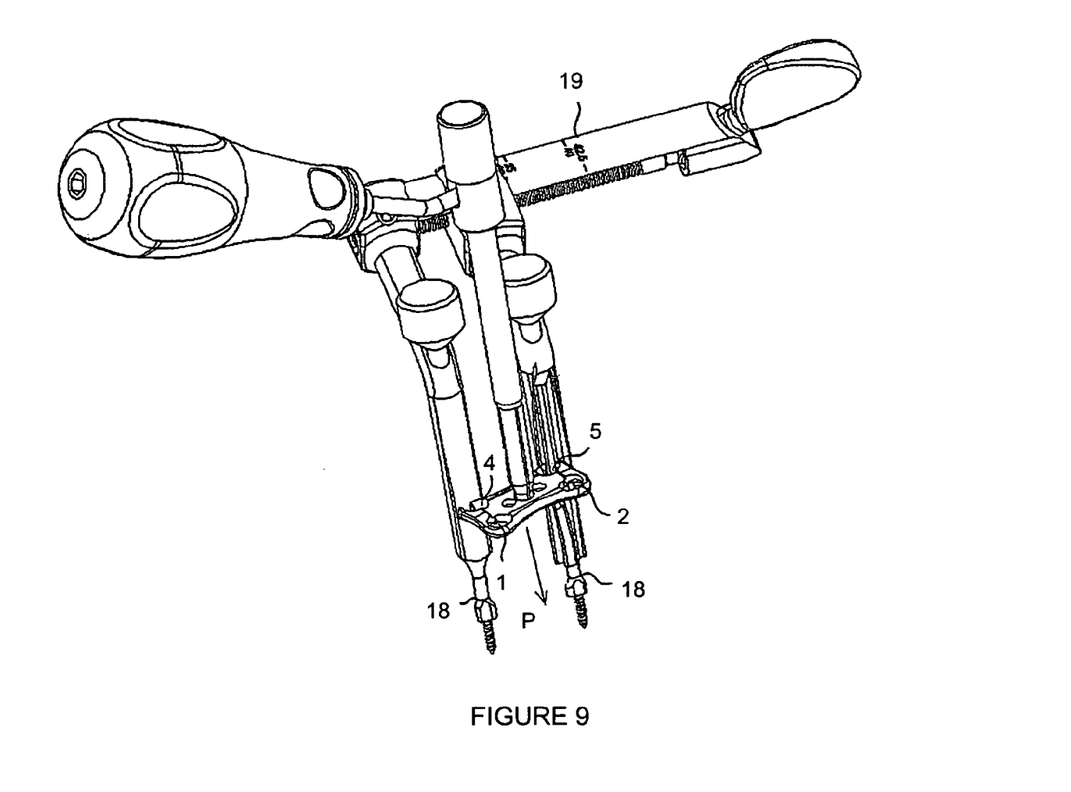
FIG. 9 represents a perspective view of the positioning phase of the vertebral osteosynthesis plate according to the invention.

The screws or rods positioned for realignment remain in position, and the plate is positioned along the positioning arrow P, as illustrated in FIG. 9, by threading the slots 4, 5 on the correction rods 18. The plate is then applied to the vertebrae.

The size of the plate to be inserted is advantageously indicated on a reading rule of the correction instrument.

Figure 10:
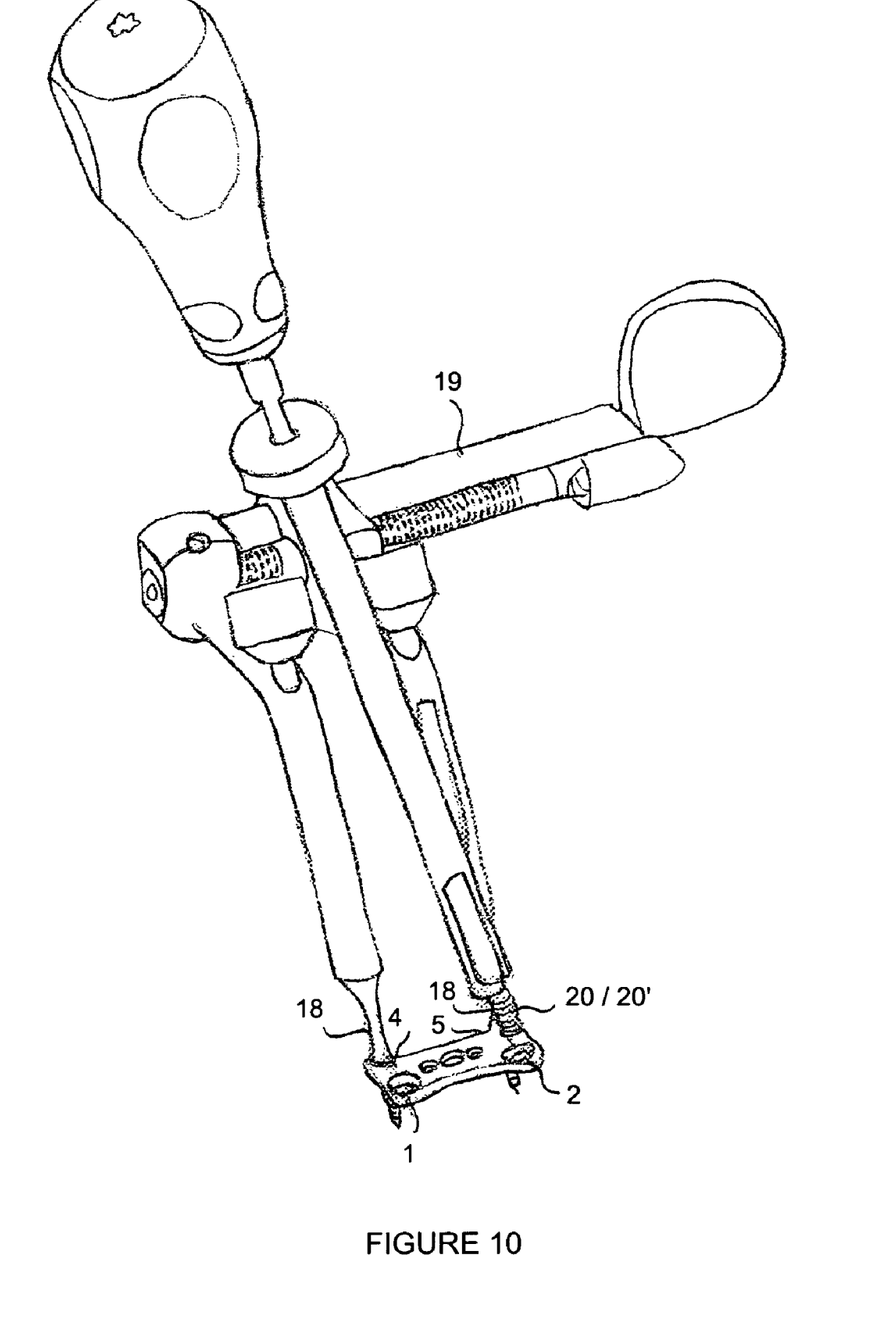
FIG. 10 represents a perspective view of the fixation phase of the vertebral osteosynthesis plate according to the invention.

Then, the vertebral osteosynthesis plate is fixed with bone fixation screws 20 or 20', inserted into the slots 1, 2, as illustrated in FIG. 10. During this operation, the vertebral alignment is held in place by the correction rods 18 and prevents any risk of the force exerted on the bone graft being released.

The correction instrument 19 can then be removed from the lateral slots 4, 5. The positioning of the bone fixation screws inserted in the slots 1, 2 makes it possible, after the removal of the correction rods and the adjustment instrument, to maintain the compression force applied on the bone graft or the interbody cage.

Bone fixation screws 20 or 20' can then be positioned in the slots 4, 5, in order to perfect the fixation of the vertebral osteosynthesis plate.

Then, the covering plate 14 is fixed onto the vertebral osteosynthesis plate.

Maintaining the compression throughout the positioning of the plate proves to be beneficial for the patient.

In addition, maintaining the compression of the graft or interbody cage after the positioning of the plate appears to enable more rapid and more effective bone fusion and prevents the migration of the graft or interbody cage.

The correction instrument 19 according to the invention can be used, by means of a compression/distraction inversion system 30, to invert the correction and produce a compression or distraction on said vertebrae, is illustrated in FIGS. 11 to 16.

Figure 11:
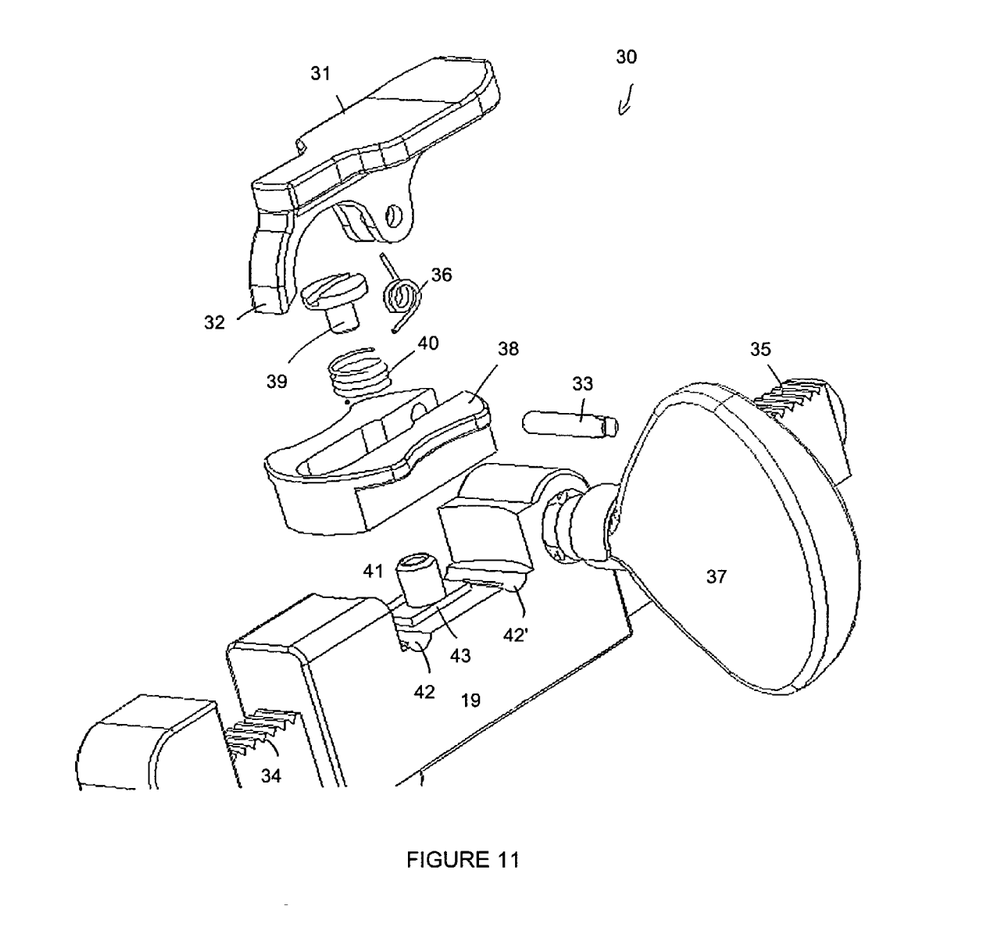
FIG. 11 represents an exploded perspective view of the correction instrument compression/distraction inversion system.
Figure 12:
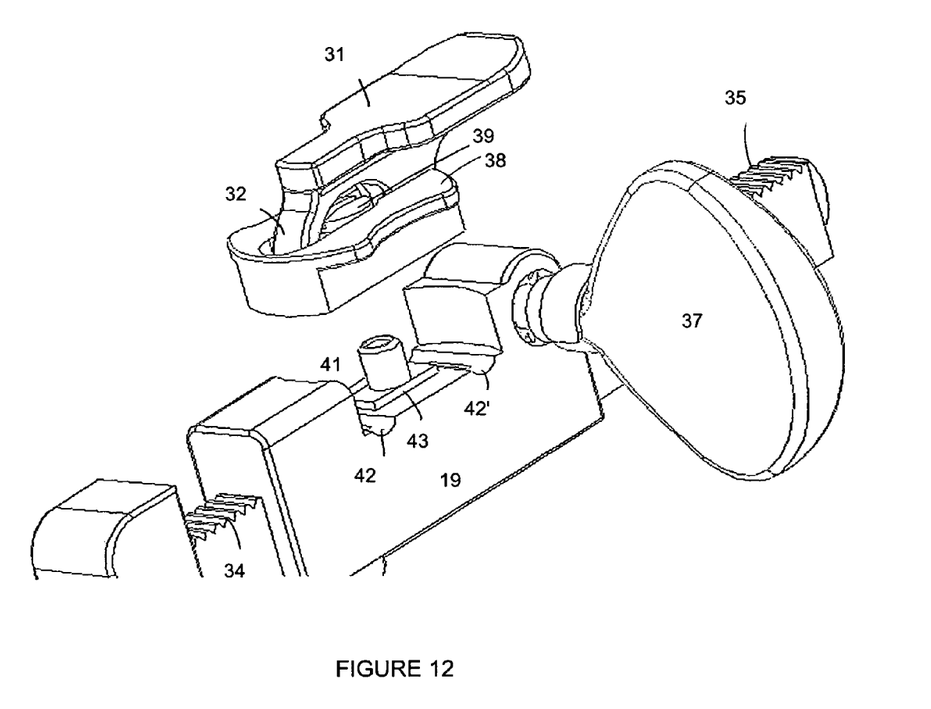
FIG. 12 illustrates a view of the system in FIG. 11 in the assembly position.

The inversion system 30 is composed of a catch 31, comprises an arm 32 and is mounted mobile onto an axis 33. The end of the arm 32 of the catch 31 is retracted to the contact position with the hollow of the teeth 34 of a rack 35 using a spring 36.

The rack may be moved forwards or backwards (according to the compression or distraction position of the inversion system 30) using a mobile button 37 rotating along an axis roughly perpendicular to said forwards/backwards direction and equipped with a toothed wheel (not shown), wherein the teeth can co-operate with the teeth 34 of the rack 35.

The axis 33 is positioned in a support 38, which is fixed on the instrument 19 using a screw 39 comprising, under its head, a space for the positioning of a helical spring 40.

In addition, the instrument 19 comprises a cavity 41 wherein a screw pitch is provided to be able to fasten the screws 39 and also comprising two holes 42, 42' to insert the arm 32 of the catch 31.

The cavity 41 also comprises a guide 43 to guide the orientation of the support 38.

Figure 13:
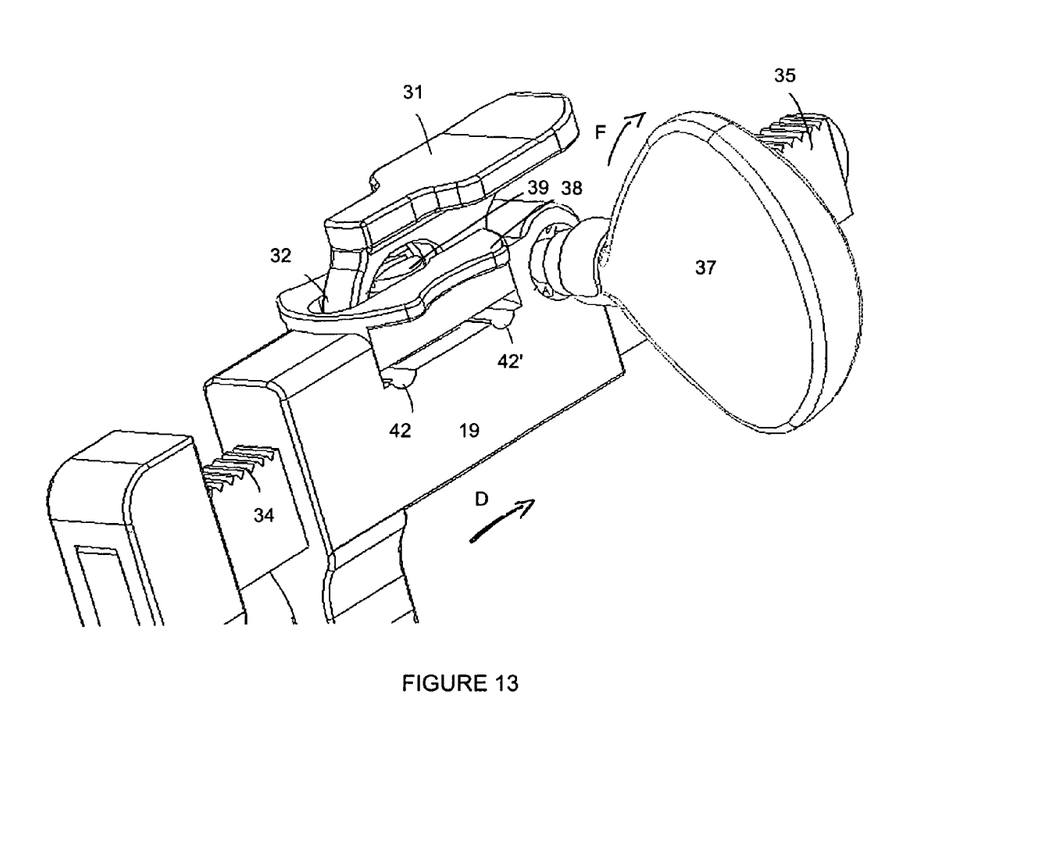
FIG. 13 illustrates a view of the system in FIG. 11 assembled to produce a distraction.

To produce a distraction D, it is simply necessary to turn the button 37 in the direction of the arrow F, as illustrated in FIG. 13. The end 32 of the catch located in the hole 42 can be raised to enable the rack 35 to move forwards and lowered, by means of the spring 36, to prevent it from moving back.

Figure 14:
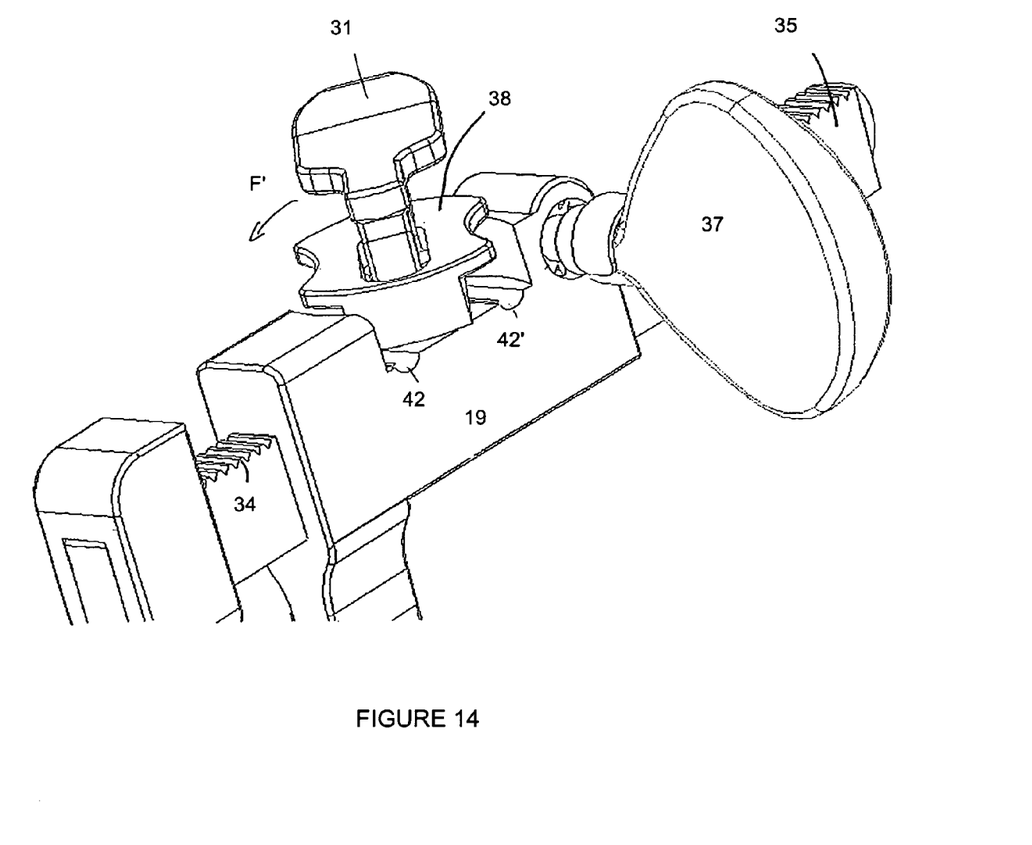
FIG. 14 illustrates a view of the system in FIG. 11 at the start of the force direction modification position.
Figure 15:
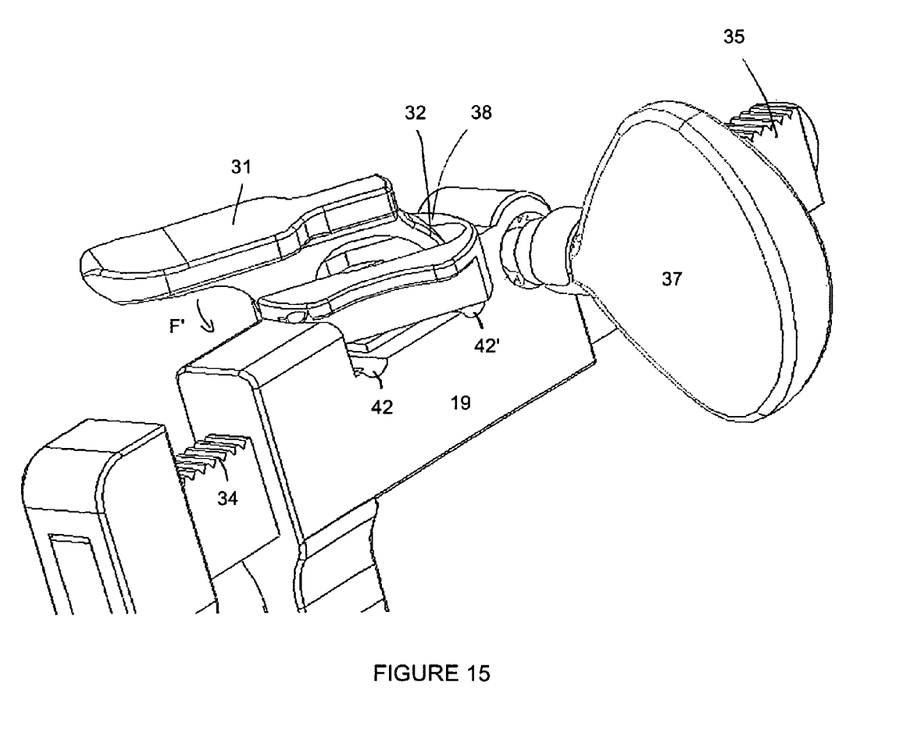
FIG. 15 illustrates a view of the system in FIG. 11 in the force direction modification position.

To change the direction of the force applied by the correction rods 18, it is necessary to raise the support 38, compressing the spring 40, in order to release the support 38 of the guide 43 and turn said support in the direction shown, for example, by the arrow F' in FIGS. 14 and 15, or in the opposite direction.

Figure 16:
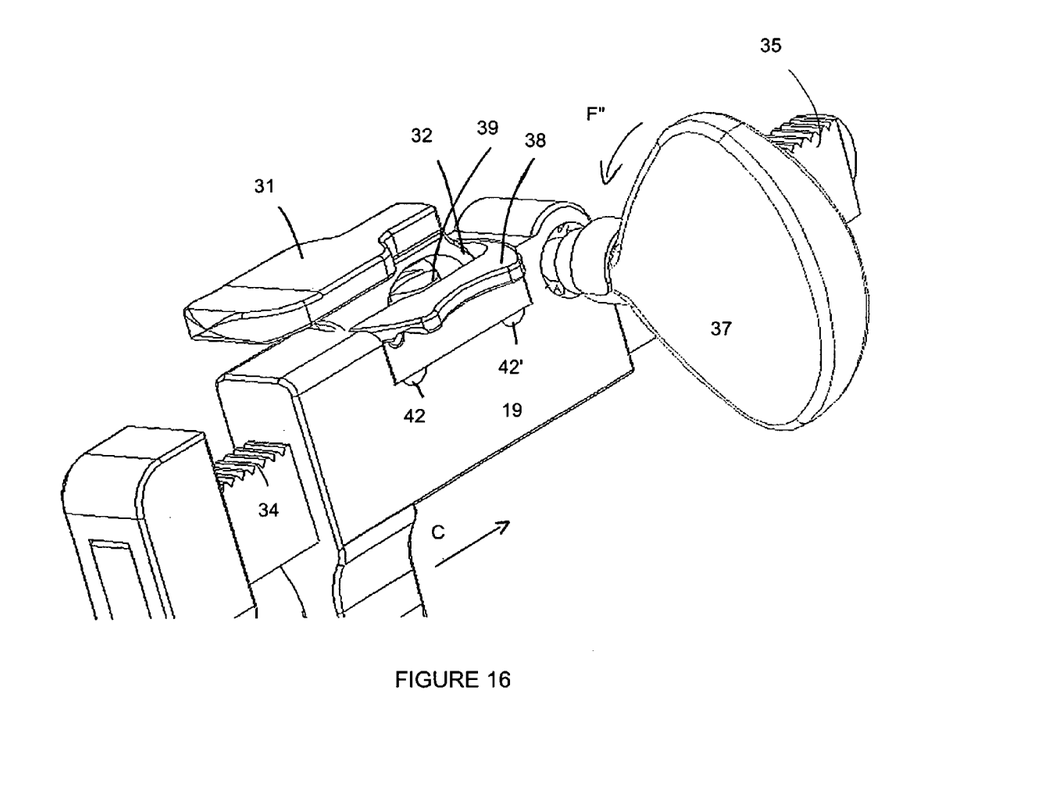
FIG. 16 illustrates a view of the correction instrument system used to invert the correction, assembled to produce a compression.

To produce a compression C, it is simply necessary to turn the button 37 in the direction of the arrow F", as illustrated in FIG. 16. The end 32 of the catch located in the hole 42 can be raised to enable the rack 35 to move forwards and lowered, by means of the spring 36, to prevent it from moving back.

What is claimed is:

1. Vertebral osteosynthesis plate to maintain relative vertebral orientation correction using a correction instrument, said osteosynthesis plate having an overall rectangular shape and comprising four slots, each to insert fixation means, each of said four slots being situated near a respective corner of the plate so that each corner of the plate has one of said slots situated nearby, at least two of said slots open onto a first lateral edge of said osteosynthesis plate to enable positioning and fixation of the osteosynthesis plate with no prior removal of the relative vertebral orientation correction instrument, the lateral edge of the osteosynthesis plate being defined by an edge located in a same direction as a longitudinal direction of the osteosynthesis plate, and the longitudinal direction of the osteosynthesis plate being roughly identical to a direction of a spinal column; and at least two of said slots are closed oblong shaped slots formed by an endless wall, said at least two closed oblong shaped slots being located between a second lateral edge of said osteosynthesis plate opposed to said first lateral edge and a central longitudinal axis of said osteosynthesis plate and being spaced from said second lateral edge.

2. Vertebral osteosynthesis plate according to claim 1, wherein at least one of the two slots opening onto the lateral edge has a non-linear shape, and wherein said shape is a curved shape.

3. Vertebral osteosynthesis plate according to claim 1, wherein at least one of the two slots opening onto the lateral edge has a non-linear shape, and wherein said shape is an L-shape.

4. Vertebral osteosynthesis plate according to claim 1, further comprising at least one of the slots opening onto the lateral edge further comprises a segment having an oblong shape oriented in a roughly longitudinal direction in order to enable an automatic post-operative compensation of intervertebral space compression effects.

5. Vertebral osteosynthesis plate according to claim 1, further comprising at least one additional slot provided roughly along a median longitudinal axis of said osteosynthesis plate.

6. Vertebral osteosynthesis plate according to claim 1, further comprising the slots opening onto the lateral edge of the plate having a spacing which is equivalent to an interbody distance between N vertebrae, N being an integer greater than or equal to two.

7. Vertebral osteosynthesis plate according to claim 1, wherein at least one of said slots to insert fixation means, comprises at least two insertion positions for said fixation means including one surface insertion position wherein said fixation means are roughly slanted at a fixed angle with reference to said osteosynthesis plate, and one in-depth insertion position wherein said fixation means have a slanting position at a variable angle.

8. Vertebral osteosynthesis plate according to claim 1, further comprising at least one fixation hole for a covering plate intended to at least partially cover said fixation means after fixation.

9. Vertebral osteosynthesis plate according to claim 8, wherein said covering plate is curved.

10. Vertebral osteosynthesis plate according to claim 8, wherein said covering plate has at least one co-operating fixation hole.

11. Vertebral osteosynthesis plate according to claim 10, wherein said at least one co-operating fixation hole is oblong.

12. Vertebral osteosynthesis plate according to claim 1, further comprising fixation means received in each of the four slots.

13. Vertebral osteosynthesis system comprising a plurality of vertebral osteosynthesis plates to maintain relative vertebral orientation correction using a correction instrument, said osteosynthesis plates having an overall rectangular shape with four corners, each of said plates comprising four slots, each to insert fixation means, each of said slots being situated near a corner of the plate,
at least two of said slots opening onto a first lateral edge of said osteosynthesis plate to enable positioning and fixation of the osteosynthesis plate with no prior removal of the relative vertebral orientation correction instrument,
wherein the plurality of plates comprises plates having different slot spacing to enable the selection by a surgeon of the osteosynthesis plate having slot spacing similar to an intervertebral distance of the patient's vertebrae during an operation, each osteosynthesis plate having a longitudinal direction roughly identical to a direction of the spinal column and at least two of the four slots being closed slots formed by an endless wall having an oblong shape oriented in the longitudinal direction, said at least two closed oblong shaped slots being located between a second lateral edge of said osteosynthesis plate opposed to said first lateral edge and a central longitudinal axis of said osteosynthesis plate and being spaced from said second lateral edge.

14. Vertebral osteosynthesis plate to maintain relative vertebral orientation correction using a correction instrument, said osteosynthesis plate having an overall rectangular shape and comprising four slots, each to insert fixation means, each of said four slots being situated near a respective corner of the plate so that each corner of the plate has one of said slots situated nearby,
at least two of said slots open onto a first lateral edge of said osteosynthesis plate to enable positioning and fixation of the osteosynthesis plate with no prior removal of the relative vertebral orientation correction instrument, the lateral edge of the osteosynthesis plate being defined by an edge located in a same direction as a longitudinal direction of the osteosynthesis plate, and the longitudinal direction of the osteosynthesis plate being roughly identical to a direction of a spinal column; and
at least two of said slots are closed oblong shaped slots formed by an endless wall, and wherein at least one of the slots that are closed has a longitudinal segment with an oblong shape oriented in the longitudinal direction, said at least two closed oblong shaped slots being located between a second lateral edge of said osteosynthesis plate opposed to said first lateral edge and a central longitudinal axis of said osteosynthesis plate and being spaced from said second lateral edge.

15. Vertebral osteosynthesis plate to maintain relative vertebral orientation correction using a correction instrument, said osteosynthesis plate having an overall rectangular shape and comprising four slots, each to insert fixation means, each of said four slots being situated near a respective corner of the plate so that each corner of the plate has one of said slots situated nearby,
at least two of said slots open onto a first lateral edge of said osteosynthesis plate to enable positioning and fixation of the osteosynthesis plate with no prior removal of the relative vertebral orientation correction instrument, the lateral edge of the osteosynthesis plate being defined by an edge located in a same direction as a longitudinal direction of the osteosynthesis plate, and the longitudinal direction of the osteosynthesis plate being roughly identical to a direction of a spinal column;
at least two additional ones of said slots being closed oblong shaped slots and each of said closed slots being formed by an endless wall, said at least two closed oblong shaped slots being located between a second lateral edge of said osteosynthesis plate opposed to said first lateral edge and a central longitudinal axis of said osteosynthesis plate and being spaced from said second lateral edge; and
wherein at least one of the two slots opening onto the first lateral edge comprises a first transverse segment opening onto the lateral edge and a second longitudinal segment extending from the first transverse segment and having an oblong shape oriented in the longitudinal direction.

* * * * *